United States Patent [19]
Brown

[11] Patent Number: 6,096,056
[45] Date of Patent: Aug. 1, 2000

[54] FUGITIVE STENT SECUREMENT MEANS

[75] Inventor: Brian J. Brown, Hanover, Minn.

[73] Assignee: Scimed Life Systems, Inc., Maple Grove, Minn.

[21] Appl. No.: 09/262,630

[22] Filed: Mar. 4, 1999

[51] Int. Cl.[7] .................................................. A61M 29/00
[52] U.S. Cl. ............................................ 606/194; 606/108
[58] Field of Search .................................. 606/194, 108, 606/192, 198, 1; 604/96, 101

[56] References Cited

U.S. PATENT DOCUMENTS

| | | | |
|---|---|---|---|
| 5,234,457 | 8/1993 | Andersen | 606/198 |
| 5,445,646 | 8/1995 | Euteneuer et al. | 606/198 |
| 5,536,252 | 7/1996 | Imran et al. | 604/101 |
| 5,571,135 | 11/1996 | Fraser | 606/198 |
| 5,643,278 | 7/1997 | Wijay | 606/108 |
| 5,653,691 | 8/1997 | Rupp et al. | 604/96 |
| 5,746,764 | 5/1998 | Green et al. | 606/108 |
| 5,908,448 | 6/1999 | Roberts et al. | 606/194 |
| 5,971,990 | 10/1999 | Venturelli | 606/108 |

FOREIGN PATENT DOCUMENTS

98/07390  2/1998  WIPO.

*Primary Examiner*—Michael Buiz
*Assistant Examiner*—Kevin Truong
*Attorney, Agent, or Firm*—Vidas, Arrett & Steinkraus, P.A.

[57] ABSTRACT

An assembly for delivery and deployment of an inflation expandable stent within a vessel is comprised of a catheter, an inflation expandable stent, an expandable balloon, and a fugitive stent mounting device within the balloon. The assembly is used in a method for delivering and deploying a stent.

10 Claims, 1 Drawing Sheet

FUGITIVE STENT SECUREMENT MEANS

BACKGROUND OF THE INVENTION

This invention relates to an assembly and method for delivering and deploying an expandable stent by balloon inflation, particularly within a lumen of a body vessel by means of a catheter assembly. It may be used for deploying other balloon expandable medical devices also, such as filters, grafts and occlusion devices. More specifically, this invention relates to the provision of a novel stent securement body within the stent expanding balloon to enhance the securement of the stent or medical device to the catheter assembly during intraluminal delivery of the stent to a deployment site. In accordance with this invention, the stent securement body comprises a fugitive element of the apparatus.

Stents and stent delivery assemblies are utilized in a number of medical procedures and situations and as such, their structure and function are well known. A stent is a generally cylindrical prosthesis which is introduced via a catheter into a lumen of a body, such as a vessel, in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available. Self-expanding stents must be maintained under positive external pressure in order to maintain their reduced diameter configuration during delivery of the stent to its deployment site. Inflation expandable stents (also known as balloon expandable stents) are crimped to their reduced diameter about the delivery catheter, positioned at the deployment site, and then expanded to the vessel diameter by fluid inflation of a balloon positioned between the stent and the delivery catheter. The present invention is particularly concerned with delivery and deployment of balloon expandable stents.

In advancing a balloon expandable stent through a body vessel to the deployment site, the stent must be able to securely maintain its axial position on the delivery catheter.

In positioning a balloon expandable stent on the delivery catheter over the fluid expandable balloon, the stent must be crimped to closely conform to the overall profile of the catheter and the unexpanded balloon.

It is known to make use of a mounting body, positioned about the catheter and within the balloon to provide a seat for the crimped stent. The application of securement pressure to the mounting body component of a catheter assembly provides a good friction fit to the stent and ensures good contact between the stent and the underlying balloon, mounting body and catheter, as already known in the art. The desired diameter of the stent upon the application of securement pressure to the mounting body and crimping recoil is characterized as the "delivery diameter", because in this condition the stent can safely, reliably and securely be delivered to the pre-selected position within a body vessel. Instead of merely crimping the stent onto the balloon and the underlying catheter and relying on the bulk of the flaccid balloon to hold the stent on, according to the present invention, the mounting body serves as a mounting base.

There are two basic functions to a mounting body. 1) It provides solid underlying material to which to crimp the stent, and 2) it may be shaped or configured to create a mechanical interference fit against axial movement of the stent. However, the presence of the mounting body on the catheter limits the catheter profile or diameter when the balloon is deflated following stent implantation.

SUMMARY OF THE INVENTION

According to the present invention, a novel, fugitive stent securement tube, ring, rings or other body, herein collectively referred to as a "mounting body", is/are positioned within the expandable balloon to aid in securing the stent to the balloon and the catheter during delivery.

Accordingly, the present invention comprises an improved assembly for delivery and deployment of an inflation expandable stent within a vessel. The assembly comprises a catheter, a fugitive mounting body carried on the catheter, an expandable balloon mounted on the catheter and encompassing the mounting body and a stent mounted on the balloon. The catheter has proximal and distal ends. The stent is inflation expandable from a delivery diameter to a deployment diameter. The delivery diameter is reduced from the manufactured diameter for conforming the stent to the catheter. The stent, in its delivery diameter, is coaxially mounted on the catheter near the catheter distal end. The expandable balloon is coaxially mounted on the catheter axially within the stent. The balloon is designed and adapted for expansion of the stent from the delivery diameter to the deployment diameter upon application of fluid deployment pressure to the balloon. The mounting body is coaxially mounted on the catheter, axially within the expandable balloon. The mounting body is preferably substantially equal in length to the stent and the stent is positioned on the assembly preferably coextensive with the mounting body. However, it may be of different size and configurations.

The mounting body is fugitive in that it is made of a softenable, more preferably a dissolvable or biodegradable material, which will remain solid up to deployment of the stent, but will soften or dissolve thereafter. The fugitive nature of the mounting body is important in allowing for the minimization of the diameter size or lower profile of the balloon/catheter for ease of withdrawal after the stent has been deployed.

In another aspect, this invention comprises a method for delivering and deploying a stent using an assembly as just described. A catheter is provided having proximal and distal ends. An expandable balloon is coaxially mounted on the catheter. A fugitive mounting body is coaxially mounted on the catheter, axially within the expandable balloon. The balloon is initially in an unexpanded condition. A stent is provided which is expandable from a delivery diameter to a deployment diameter. The stent, in a diameter greater than the delivery diameter, is initially mounted on the balloon. The stent is then collapsed to the delivery diameter to conform to an overall profile of the catheter, the mounting body and the balloon. The mounting body provides a mounting base for the balloon/stent in the delivery diameter. The assembly is delivered to a deployment site. The balloon is inflated to expand the stent to its deployment diameter. The mounting body remains solid through delivery of the stent to the lesion site. Upon inflation of the balloon, the bulk material of the mounting body softens or more preferably dissolves in the saline/contrast solution or other fluid used to inflate the balloon thus allowing for a minimal low profile when the balloon is deflated.

DETAILED DESCRIPTION OF THE INVENTION

Figure 1:
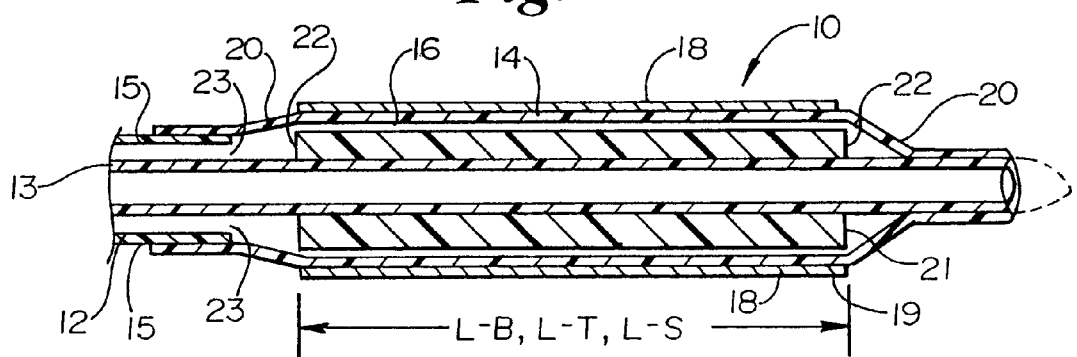
FIG. 1 is a side profile longitudinal section view showing the distal end of a balloon expandable stent delivery and deployment catheter assembly, with the stent crimped to a delivery diameter onto the balloon, the underlying mounting body providing securement of the stent; the view being schematic in that the crimped stent is not shown seated to the mounting body for clarification of illustration.

FIG. 1 illustrates a side profile section showing the distal end portion of an inflation expandable stent delivery and deployment assembly generally designated 10. Assembly 10 includes a catheter 12 preferably comprised of inner shaft 13 and outer shaft 15 of the coaxial type, an inflation expandable balloon 14, a mounting body 16 and an inflation expandable stent 18. Any conventional type of catheter may be used, such as a catheter of the type generally used for PTA or PTCA angioplasty procedures, for prostate therapy, and TTS endoscopic catheters for gastrointestinal use. However, coaxial types as shown are most preferred. The particular catheter 12 shown is formed of a biocompatible and hydrophilic compatible material, such as a lubricous polyimide or polyethylene. Other suitable materials for the catheter 12 include nylons, urethanes, and polypropylene materials compatible with coatings such as silicone and/or hydrophilic coatings. In addition to hydrophilic compatible materials, any biocompatible material may be used. For example, polyethylene or polypropylene can be coated with a hydrophilic material to render them hydrophilic compatible. Suitable catheters for use according to the present invention include a number of catheters available from SciMed Life Systems, Inc., Maple Grove, Minn., the assignee of the present invention, such as RANGER™, BANDIT™, COBRAT™, VIVA™, and VIVA PRIMO™ catheters.

Mounting body 16 surrounds inner shaft 13 at a position to be encompassed within the distal and proximal ends of the outer balloon 14. Although FIG. 1 purports to show stent 18 crimped to balloon 14 and mounting body 16, this is not the case for purposes of clarification and illustration. Those familiar with the art will understand this and will further understand what an actual crimped stent looks like on a catheter assembly. As already indicated, there may be more than one mounting body and they may be of different configurations.

Figure 2:
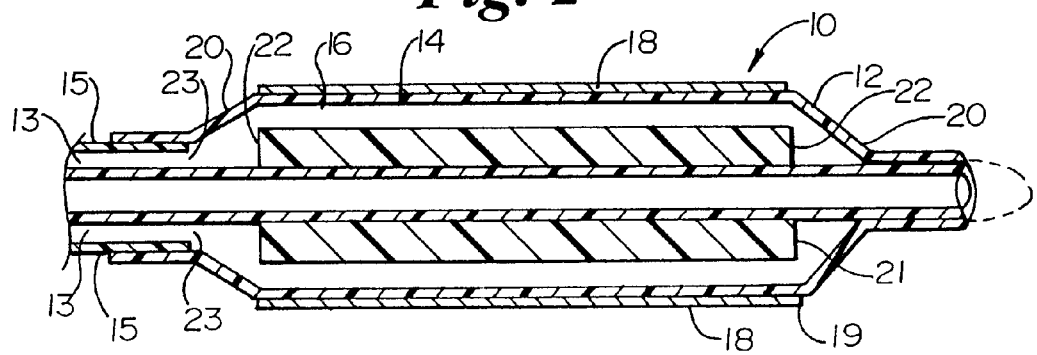
FIG. 2 is a schematic side profile section, similar to FIG. 1, with the balloon and the stent inflated to deployment diameter.

According to art-recognized convention, the length L-B of the balloon 14 is defined as the length of the body portion of the balloon 14, excluding the balloon terminal cone sections 20. As seen in FIG. 2, the body portion of the balloon 14 is generally cylindrical when in its inflated condition. Mounting body 16 is illustrated as having end surfaces 22 which are more relatively vertical than the cone sections 20 illustrated for the balloon 14. However, it is to be understood that, according to the present invention, either of the end surfaces 20, 22 may be relatively cone shaped, relatively vertical or of any other configuration desired or known to those of skill in this art. A preferred length L-T of the mounting body 16 is illustrated in FIGS. 1 and 2 as substantially equal to the length L-B of balloon 14, and substantially equal to the length L-S of stent 12. However, according to the present invention, stent 12 may be supported by the underlying mounting body 16 for any length and in any number of configurations sufficient to permit accomplishment of the stated purpose of the mounting body 16, i.e., to provide securement for stent 18 and to maintain stent 18 in position on assembly 10 during delivery. It is also within the present invention for mounting body 16 to be shorter than stent 12. For example, the distal end 19 of stent 18 may extend distally beyond the distal end 21 of mounting body 16, so that distal end 19 of stent 18 can be crimped over the distal end 21 of mounting body 16 to prevent the distal end 19 of stent 18 from catching and tending to further open as it is maneuvered within a body vessel.

Mounting body 16 is preferably dissolvable or biodegradable and may be made of water soluble materials such as gelatin, polyacrylic acid, polymethacrylic acid, polypropyl alcohol, polysaccharides, polyethyleneoxide (PEO), polyvinylpyrrolidone (PVP); polyvinyl alcohol (PVA); mannitol, complex carbohydrates, salts or the like. Should the mounting body comprise a continuous tube comprised of sections, more than one tube or a series of bands, the composition of sections, separate tubes or individual bands can be varied as desired, for instance to vary the dissolution rate of such bands. This can also be accomplished by varying the molecular weights of the compositions, since the lower the molecular weight the faster a band will dissolve. Varying the thickness of a section or band or adding perforations thereto will also increase the rate of dissolution.

As previously stated, the mounting body may be merely softenable so as to allow a low profile on deflation of the balloon. Hydrogels are adequate for such an embodiment.

A balloon 14 for use according to the present invention may be any conventional balloon for catheter delivery, such as a balloon of the type generally used for PTA and PTCA procedures. Typically, balloon 14 is fixed at its distal end to inner shaft 13 near the catheter distal end and at its proximal end to outer shaft 15.

Balloon 14 is larger in diameter than mounting body 16 in the embodiment shown, and is inflatable through an inflation conduit 23, i.e., the space between coaxial inner shaft 13 and outer shaft 15 of the catheter. The distal and proximal ends of balloon 14 are shown in FIGS. 1 and 2 positioned exterior to the distal and proximal ends of mounting body 16, respectively, and of a length L-B generally equal to the length L-T of mounting body 16. As shown at FIG. 2, balloon 14 is inflatable at deployment to about the diameter of the body vessel in which the stent 18 is to be deployed. This particular arrangement, although preferred, may be varied.

Balloon 14 may be formed of either compliant or non-compliant balloon materials. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers. Suitable materials include a copolymer polyolefin material available from E.I. DuPont de Nemours and Co. (Wilmington, Del.), under the trade name Surlyn™ Ionomer and a polyether block amide available under the trade name PEBAX™. Non-compliant materials include relatively rigid of stiff high pressure polymeric materials, such as thermoplastic polymers and thermoset polymeric materials, poly (ethylene terephthalate) (commonly referred to as PET), polyimide, thermoplastic polyimide, polyamides, polyesters, polycarbonates, polyphenylene sulfides, polypropylene and rigid polyurethanes.

A stent for use according to the present invention may be any conventional type of balloon expandable stent, including stents of the type used for PTA and PTCA angioplasty procedures, for prostate therapy, and TTS endoscopic catheters for gastrointestinal use. Stent 18 as shown in FIGS. 1 and 2 is positioned on balloon 14, the underlying mounting body 16 and the distal end of the catheter. The length L-S of stent 18 is shown as essentially equal or slightly smaller than the length L-T of mounting body 16 and is positioned on assembly 10 to be co-extensive with mounting body 16. In this position, stent 18 may be crimped to its delivery diameter D1.

FIG. 2 illustrates a side profile section showing a stent delivery and deployment assembly 10 of this invention with balloon 14 fluid inflated. As a result of the fluid inflation of the balloon 14, stent 18 has also been expanded to its deployment diameter D2 in which it can be deployed against the walls of a body vessel in which it is situated (not shown).

Mounting body 16 may have a shape other than the cylindrical shape described and illustrated with regard to the embodiment shown in FIGS. 1 and 2. For example, the mounting body may comprise a ring or a series of individual rings.

The method of using the stent delivery and deployment assembly 10 of this invention, as shown in FIGS. 1 and 2, is described as follows. The assembly 10 is constructed as described above. Stent 18 is compressed or crimped onto balloon 14, mounting body 16 and the catheter to a delivery diameter D1. This crimping can be done manually or with the aid of tooling specially designed for the purpose either by the physician or the manufacturer. In the crimped position, stent 18 closely conforms to the overall profile of balloon 14, and the catheter 12 and provides against axial movement on the catheter.

Figure 3:
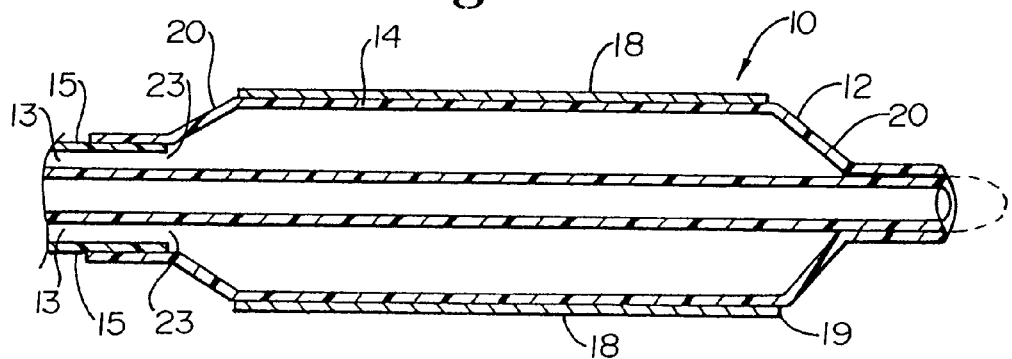
FIG. 3 is a view similar to FIGS. 1 and 2 showing an inflated balloon and expanded stent with the mounting body dissolved.
Figure 4:
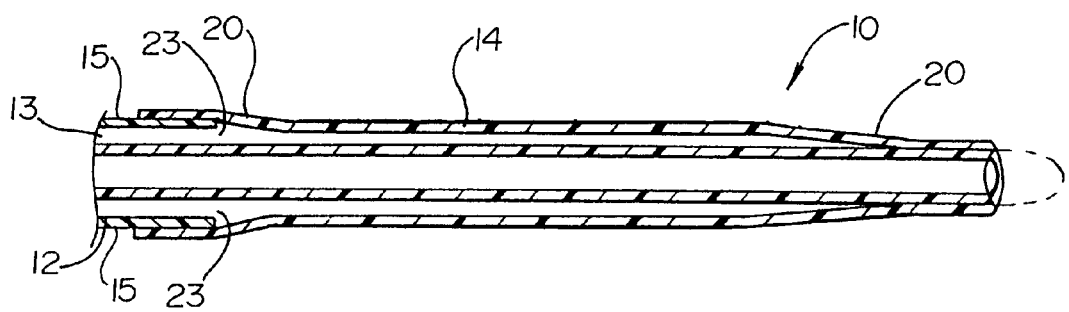
FIG. 4 is a view similar to FIGS. 1 and 2 showing a deflated balloon with the mounting body dissolved to provide a minimal low catheter assembly profile for withdrawal from the body.

The catheter distal end is delivered by standard techniques to the deployment site within the body vessel of interest. The material of which mounting body 16 is made will remain solid during the negative purge and delivery to the deployment site. At this point, stent 18 is positioned as required by the physician and balloon 14 is fluid inflated by standard technique to expand stent 18 to its deployment diameter D2. During this expansion, stent 18 is expanded to fill the body vessel. Also during this expansion, mounting body 16 comes in contact with the fluid for inflation, which may be saline and/or contrast solution, and will dissolve in the fluid as shown in FIG. 3. Thus, the term fugitive is applied to describe the mounting body. Following deployment of stent 12, balloon 14 is deflated to low profile as shown in FIG. 4 and the assembly 10 is retracted proximally and withdrawn from the body. If required by the procedure, the site of entry to the body is appropriately closed.

The advantages provided by the softenable, dissolvable or biodegradable material (herein collectively referred to as "fugitive") for the mounting body include but are not limited to the following. In many cases, the securement of a stent to a balloon is facilitated by material built up between the inner shaft outer diameter and the balloon inner diameter. This material adds bulk to the system which the stent is able to crimp onto, but this added bulk also limits the reuse of the delivery balloon as an adjunctive post delivery balloon that needs to retrack down to the lesion and stent deployment site. The inventive mounting body of fugitive material provides a way to have the bulk material present during stent delivery but removed during follow up use. The mounting body made of softenable, dissolvable or biodegradable material will remain solid during the negative purge and delivery to the lesion site but will soften or dissolve in the expansion fluid (saline/contrast solution) upon inflation of the balloon.

The mounting body provided by this invention maximizes stent securement force by optimizing the frictional force between the balloon and the internal diameter of the stent in its reduced crimped delivery diameter. The features and principles described for this invention are suitable for use with fixed wire, over-the-wire and monorail assemblies.

The above Examples and disclosure are intended to be illustrative and not exhaustive. These examples and description will suggest many variations and alternatives to one of ordinary skill in this art. All such alternatives and variations are intended to be included within the scope of the attached claims. Those familiar with the art may recognize other equivalents to the specific embodiments described herein which equivalents are also intended to be encompassed by the claims attached hereto.

What is claimed is:

1. In a medical device delivery apparatus of the type for percutaneous delivery and implantation of a medical device, the apparatus comprising;

a balloon catheter including an elongate tubular body defining proximal and distal extremities;

an inflation lumen extending from the proximal extremity to the distal extremity;

an inflatable balloon carried at the distal extremity and coaxially disposed with respect to the distal extremity and in fluid communication with the inflation lumen;

medical device mounting means on the distal extremity and internal to the balloon, coaxially disposed with respect to the distal extremity, the mounting means being of a predetermined configuration and size, and a medical device mounted coaxially upon the balloon and mounting means, the improvement comprising wherein the medical device mounting means is comprised at least in part of a material dissoluble upon exposure to fluid.

2. The apparatus of claim 1 wherein the mounting means is dissoluble upon exposure to the balloon inflating fluid.

3. The apparatus of claim 1 wherein the medical device mounting means is comprised at least in part of a water soluble material.

4. The apparatus of claim 1 wherein the medical device is a stent.

5. The apparatus of claim 4 wherein the mounting means is a body essentially equal in length to the stent and wherein the stent is positioned on the assembly essentially coextensive with the body.

6. The apparatus of claim 1 wherein the mounting means comprises at least two individual rings.

7. A method for delivering and deploying a stent using an assembly according to claim 1, comprising:

providing a catheter having proximal and distal ends, with an expandable balloon coaxially mounted on the catheter, and a mounting means coaxially mounted on the catheter and axially within the expandable balloon, the balloon being in an unexpanded condition;

providing a medical device which is expandable from a delivery diameter to a deployment diameter;

mounting the medical device, in a diameter greater than the delivery diameter, on the balloon;

contracting the medical device to the delivery diameter to conform to an overall profile of the catheter, the mounting means and the balloon;

delivering the assembly to a deployment site; and inflating the balloon to expand the medical device to its deployment diameter.

8. The method of claim 7 wherein the medical device is a stent.

9. The method according to claim 7, wherein the balloon is in communication with a source of inflation fluid, the mounting means is made of a dissolvable or biodegradable material, said mounting means being constructed and arranged to dissolve in said inflation fluid, and upon inflation of the balloon, the mounting means component dissolves in the inflation fluid.

10. The method according to claim 9 wherein the inflation fluid comprises a saline contrast solution.

* * * * *